United States Patent
Ueda et al.

(10) Patent No.: US 10,485,480 B2
(45) Date of Patent: Nov. 26, 2019

(54) PROBE

(71) Applicant: NIHON KOHDEN CORPORATION, Tokyo (JP)

(72) Inventors: Yoshinori Ueda, Tokyo (JP); Teiji Ukawa, Tokyo (JP); Kazumasa Ito, Tokyo (JP); Hideki Fujisaki, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 421 days.

(21) Appl. No.: 15/207,581

(22) Filed: Jul. 12, 2016

(65) Prior Publication Data

US 2017/0014076 A1 Jan. 19, 2017

(30) Foreign Application Priority Data

Jul. 17, 2015 (JP) .................. 2015-142992

(51) Int. Cl.
*A61B 5/1455* (2006.01)
*A61B 5/00* (2006.01)
*A61B 5/024* (2006.01)

(52) U.S. Cl.
CPC .......... *A61B 5/6826* (2013.01); *A61B 5/0059* (2013.01); *A61B 5/6838* (2013.01); *A61B 5/02427* (2013.01); *A61B 5/14552* (2013.01); *A61B 2562/16* (2013.01)

(58) Field of Classification Search
CPC . A61B 5/6826; A61B 5/0059; A61B 5/14552; A61B 5/6838; A61B 5/1455; A61B 5/02427; A61B 2562/16
See application file for complete search history.

(56) References Cited

U.S. PATENT DOCUMENTS 4,685,464 A  8/1987  Goldberger et al.
6,608,562 B1  8/2003  Kimura et al.
(Continued)

FOREIGN PATENT DOCUMENTS

JP  2001-000422 A  1/2001
JP  2001-070266 A  3/2001
(Continued)

OTHER PUBLICATIONS

Extended European Search Report issued in Patent Application No. EP 16 17 8978 dated Dec. 19, 2016.
(Continued)

*Primary Examiner* — Eric F Winakur
(74) *Attorney, Agent, or Firm* — Pearne & Gordon LLP

(57) ABSTRACT

A probe which is to be attached to a finger of a subject to acquire physiological parameter of the subject includes a light emitter that emits a light beam toward the finger, a light detector that outputs a signal corresponding to a light beam that is transmitted through or reflected from the finger, a first holding face that has a portion which is faced with a nail of the finger and another portion which is faced with a side face of the finger, and a second holding face that has a portion which is faced with a pad of the finger and another portion which is faced with the side face of the finger. In a state where the probe is attached to the finger, the first holding face and the second holding face are placed to be continuous to each other.

16 Claims, 2 Drawing Sheets

(56) References Cited

U.S. PATENT DOCUMENTS

| | | | | |
|---|---|---|---|---|
| 6,801,798 B2* | 10/2004 | Geddes | ............... | A61B 5/02233 |
| | | | | 600/323 |
| 2001/0009265 A1* | 7/2001 | Schulz | ............... | A61B 5/02427 |
| | | | | 250/227.14 |
| 2003/0023171 A1* | 1/2003 | Sato | ................... | A61B 5/14552 |
| | | | | 600/476 |
| 2010/0105996 A1* | 4/2010 | Segman | ............... | A61B 5/0205 |
| | | | | 600/322 |
| 2010/0168531 A1* | 7/2010 | Shaltis | ............... | A61B 5/02241 |
| | | | | 600/301 |
| 2013/0345533 A1* | 12/2013 | Jungmann | ............ | A61B 5/1455 |
| | | | | 600/344 |
| 2015/0230755 A1* | 8/2015 | Al-Ali | ................. | A61B 5/6838 |
| | | | | 600/324 |

FOREIGN PATENT DOCUMENTS

| | | | |
|---|---|---|---|
| JP | 2007029702 A | 2/2007 | |
| JP | 2007-167183 A | 7/2007 | |
| JP | 2007-167184 A | 7/2007 | |
| JP | 2009-201918 A | 9/2009 | |

OTHER PUBLICATIONS

Japanese Office action issued in Patent Application No. JP 2015-142992 dated Mar. 5, 2019.

* cited by examiner

PROBE

CROSS REFERENCE TO RELATED APPLICATION

This application is based on Japanese Patent Applications No. 2015-142992 filed on Jul. 17, 2015, the contents of which are incorporated herein by reference.

BACKGROUND

The presently disclosed subject matter relates to a probe which is to be attached to the finger of a subject to acquire physiological parameter of the subject.

JP-A-2007-029702 discloses a probe which is to be attached to the fingertip of a subject. The probe includes a light-emitting element and a light-detecting element. The light-detecting element has a light-detecting surface which detects a light beam that is emitted from the light-emitting element, and that is transmitted through the living tissue of the fingertip. The light-detecting element outputs a signal corresponding to the intensity of the light beam which is detected by the light-detecting surface. The light beam emitted from the light-emitting element is determined to have a wavelength at which a light beam is to be absorbed by a material in blood. The volume of blood in the fingertip is changed in accordance with the pulsation, and therefore also the intensity of the light beam which is detected by the light-detecting surface is changed. The signal output from the light-detecting element is used for calculating physiological parameter of the subject, such as the pulsation and the arterial oxygen saturation.

In the case where the fingertip of the subject is applied with nail polish or nail art, the light beam emitted from the light-emitting element may be absorbed by coloring matter of the nail polish or the nail art. In this case, there is a possibility that the light-detecting element may fail to detect a desired amount of light, and this may pose obstacles to calculation of physiological parameter.

The trouble of removing such a nail polish or nail art may cause a delay in taking a countermeasure in an emergency situation. On the other hand, such a nail polish or nail art includes expensive ones, and hence there is a need for, in a non-emergency situation, performing calculation of physiological parameter without removing a nail polish or nail art.

It is an object of the presently disclosed subject matter to enable physiological parameter to be accurately calculated regardless of presence or absence of a nail polish or nail art.

SUMMARY

According to an aspect of the presently disclosed subject matter, a probe which is to be attached to a finger of a subject to acquire physiological parameter of the subject includes a light emitter that emits a light beam toward the finger, a light detector that outputs a signal corresponding to a light beam that is transmitted through or reflected from the finger, a first holding face that has a portion which is faced with a nail of the finger and another portion which is faced with a side face of the finger, and a second holding face that has a portion which is faced with a pad of the finger and another portion which is faced with the side face of the finger. In a state where the probe is attached to the finger, the first holding face and the second holding face are placed to be continuous to each other.

According to the above configuration, the light emitter and the light detector are easily placed at positions (such as side face of the finger) avoiding the nail. Therefore, physiological parameter can be accurately calculated regardless of presence or absence of a nail polish or nail art.

Particularly, the first holding face having the portion which is faced with the nail extends to a position which is faced with a side face of the finger, and is continuous to the second holding face having the portion which is faced with the pad. Therefore, ambient light can be suppressed from entering the light emitter and light detector which are placed at the above-described positions, respectively. Consequently, the accuracy of calculation of physiological parameter can be prevented from being lowered.

DETAILED DESCRIPTION OF EMBODIMENTS

Figure 1A:
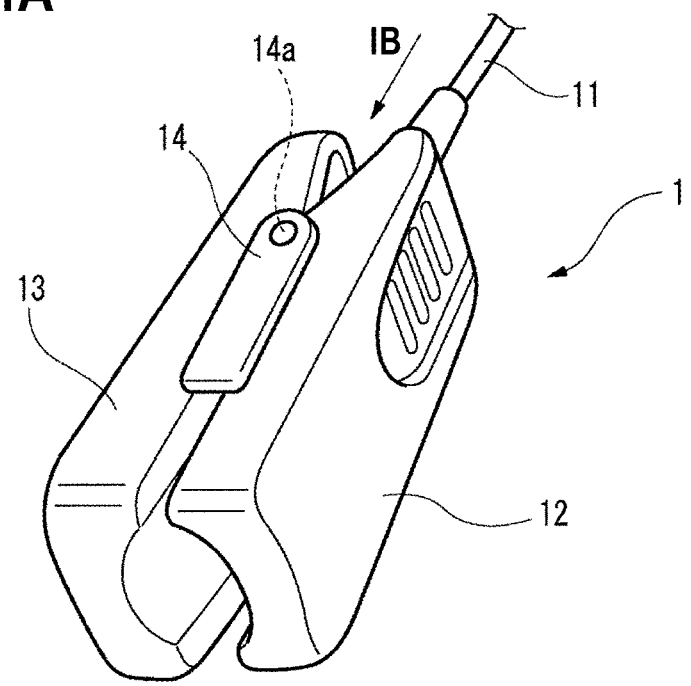
FIGS. 1A and 1B illustrate a probe of an embodiment.

An embodiment will be described in detail with reference to the accompanying drawings. In the drawings described in the specification, in order to make the components to have a recognizable size, their scales are appropriately changed.

FIG. 1A is a perspective view illustrating the appearance of a probe 1 of the embodiment. In order to acquire physiological parameter of a subject, the probe 1 is attached to the finger of the subject. The finger may be a finger or a thumb of the hand or a toe of the foot. Examples of physiological parameter are the pulsation and the arterial oxygen saturation.

The probe 1 may include a cable 11, a left side portion 12, a right side portion 13, and a hinge portion 14. The probe 1 is connected to an external measuring apparatus (not shown) through the cable 11. Examples of the measuring apparatus are a bedside monitor and a pulse photometer.

Figure 1B:
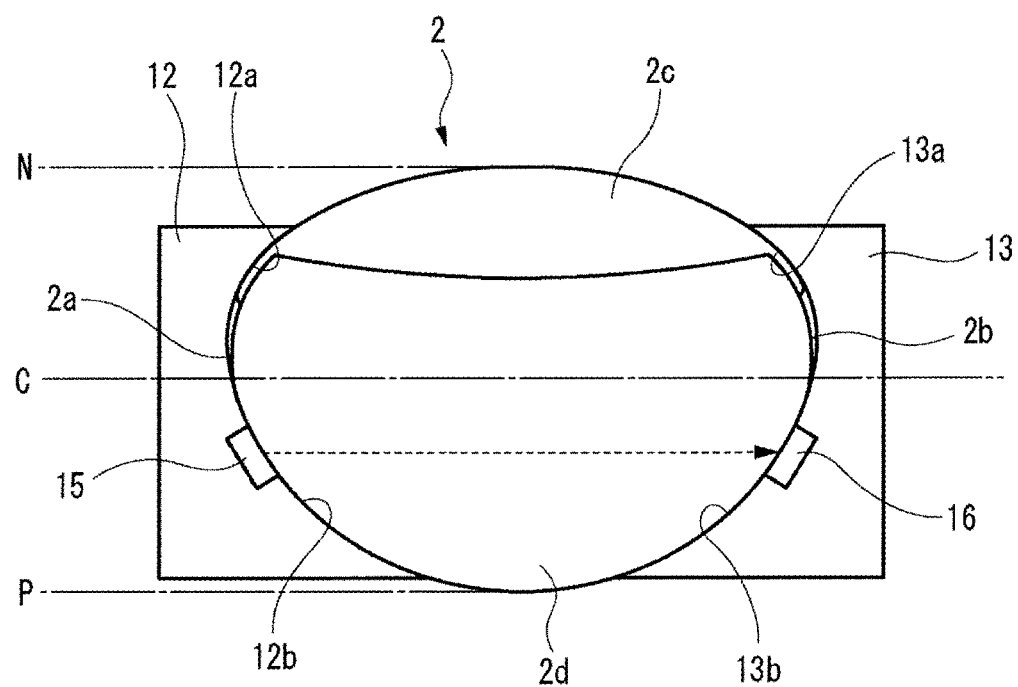

FIG. 1B diagrammatically illustrates sectional shapes of the left and right side portions 12, 13 as viewed in the direction of the arrow IB (i.e., from the fingertip side) in FIG. 1A in a state where the probe 1 is attached to the finger 2 of the subject. In the following description, "left" and "right" mean directions as viewed from the fingertip side of the subject.

The left side portion 12 is configured so as to be faceable with the left side face 2a of the finger 2. The right side portion 13 is configured so as to be faceable with the right side face 2b of the linger 2. As illustrated in FIG. 1A, the hinge portion 14 connects the left and right side portions 12, 13 together so that the gap between the side portions can be adjusted.

As illustrated in FIG. 1B, the probe 1 may further include a light emitter 15 and a light detector 16. The light emitter 15 is placed in the left side portion 12. The light detector 16 is placed in the right side portion 13.

The light emitter 15 emits a light beam having a predetermined wavelength, based on a control signal which is supplied through the cable 11. The predetermined wavelength is defined as a wavelength at which a light beam is absorbable by a material in blood. The material is determined in accordance with the kind of the physiological parameter to be calculated. In the case where the pulsation and the arterial oxygen saturation are to be calculated, for example, hemoglobin which can carry oxygen is selected as the material. In this case, a red light beam and an infrared light beam are selected as examples of the light beam having the predetermined wavelength.

For example, the light emitter 15 is a semiconductor light emitting device which can emit a light beam at the predetermined wavelength. Examples of the semiconductor light emitting device are a light emitting diode (LED), a laser diode, and an organic electroluminescence (EL) device.

The light detector 16 has a light-detecting surface which detects a light beam that is transmitted through the finger 2. The light detector 16 outputs an intensity signal in accordance with the intensity of the light beam which is detected by the light-detecting surface. The intensity signal corresponds to the physiological parameter. The volume of blood flowing through the finger 2 to which the probe 1 is attached is changed in accordance with the pulsation of the subject. Therefore, the intensity of the light beam which is detected by the light-detecting surface is changed, and also the intensity signal which is output from the light detector 16 is changed.

The signal output from the light detector 16 is transmitted to the external measuring apparatus through the cable 11. The measuring apparatus acquires a desired physiological parameter from changes of the intensity signal based on a predetermined algorithm.

For example, the light detector 16 is an optical sensor having a sensitivity to the above-described predetermined wavelength. Examples of the optical sensor are a photodiode, a phototransistor, and a photoresistor.

As illustrated in FIG. 1B, the left side portion 12 may include a nail-side left holding face 12a and a pad-side left holding face 12b. The nail-side left holding face 12a (an example of the first holding face) has a portion which is faced with the nail 2c of the finger 2, and a portion which is faced with the left side face 2a (an example of the side face of the finger) of the finger 2. The pad-side left holding face 12b (an example of the second holding face) has a portion which is faced with the pad 2d of the finger 2, and a portion which is faced with the left side face 2a of the finger 2.

As illustrated in FIG. 1B, the right side portion 13 may include a nail-side right holding face 13a and a pad-side right holding face 13b. The nail-side right holding face 13a (an example of the first holding face) has a portion which is faced with the nail 2c of the finger 2, and a portion which is faced with the right side face 2b (an example of the side face of the finger) of the finger 2. The pad-side right holding face 13b (an example of the second holding face) has a portion which is faced with the pad 2d of the finger 2, and a portion which is faced with the right side face 2b of the finger 2.

In FIG. 1B, the dash-dot line N indicates a nail-side end portion of the thickness in the direction from the nail 2c of the finger 2 to the pad 2d. The dash-dot line P indicates a pad-side end portion of the thickness in the direction from the nail 2c of the finger 2 to the pad 2d. The dash-dot line C is an intermediate line which is equidistant from the dash-dot lines N, P. In the specification, the area between the dash-dot line N and the dash-dot line C is defined as "nail side" of the finger 2, and the area between the dash-dot line P and the dash-dot line C is defined as "pad side" of the finger 2.

Based on this definition, it is assumed that the boundary between the nail-side left holding face 12a and the pad-side left holding face 12b is at the position where the dash-dot line C intersects with the left side portion 12. It is also assumed that the boundary between the nail-side right holding face 13a and the pad-side right holding face 13b is at the position where the dash-dot line C intersects with the right side portion 13.

As seen from FIG. 1B, in a state where the probe 1 is attached to the finger 2, the nail-side left holding face 12a and the pad-side left holding face 12b are placed so as to be continuous to each other. In the state where the probe 1 is attached to the finger 2, furthermore, the nail-side right holding face 13a and the pad-side right holding face 13b are placed so as to be continuous to each other.

According to the configuration, the light emitter 15 and the light detector 16 are easily placed at positions avoiding the nail 2c. In the embodiment, for example, the light emitter 15 is placed at a position where it is faced with the left side face 2a of the finger 2, and the light detector 16 is placed at a position where it is faced with the right side face 2b of the finger 2. Therefore, physiological parameter can be accurately calculated regardless of presence or absence of a nail polish or nail art.

Particularly, the nail-side left holding face 12a and nail-side right holding face 13a which have the portions that are faced with the nail 2c extend to positions which are faced with the left and right side faces 2a, 2b of the finger 2, and are continuous to the pad-side left holding face 12b and pad-side right holding face 13b which have the portions that are faced with the pad 2d, respectively. Therefore, ambient light can be suppressed from entering the light emitter 15 and light detector 16 which are placed at the above-described positions, respectively. Consequently, the accuracy of calculation of physiological parameter can be prevented from being lowered.

As seen from FIG. 1B, the section of the nail-side left holding face 12a as viewed from the fingertip side has a shape which extends along the nail side of the finger 2. The section of the pad-side left holding face 12b as viewed from the fingertip side has a shape which extends along the pad side of the finger 2. The sectional shape of the nail-side left holding face 12a is different from that of the pad-side left holding face 12b. Similarly, the section of the nail-side right holding face 13a as viewed from the fingertip side has a shape which extends along the nail side of the finger 2. By contrast, the section of the pad-side right holding face 13b as viewed from the fingertip side has a shape which extends along the pad side of the finger 2. The sectional shape of the nail-side right holding face 13a is different from that of the pad-side right holding face 13b.

At a position avoiding the nail 2c, usually, the outer circumferential face of the finger 2 has a large mean curvature. Therefore, it is difficult to stably position the light emitter 15 and the light detector 16 as compared with the case where at least one of the light emitter 15 and the light detector 16 is placed so as to be faced with the nail 2c. In the configuration where, as described above, the sectional shapes of the nail-side left holding face 12a and the pad-side left holding face 12b are made different from each other, and those of the nail-side right holding face 13a and the pad-side right holding face 13b are made different from each other, however, the finger 2 can be further fit into the probe 1. This facilitates stable positioning of the light emitter 15 and the light detector 16 while avoiding the nail 2c. Therefore, the accuracy of calculation of physiological parameter can be further prevented from being lowered.

More specifically, the light emitter 15 and the light detector 16 are placed so as to be faced with the pad side of the finger 2.

Depending on subjects, the nail 2c sometimes extends to the left and right side faces 2a, 2b of the finger. According to the configuration, the light emitter 15 and the light detector 16 can be placed while more surely avoiding the nail 2c. Therefore, the accuracy of calculation of physiological parameter can be further prevented from being lowered.

In the embodiment, the pad-side left holding face 12b is black in color. In the left side portion 12, for example, a portion including at least the pad-side left holding face 12b may be molded from a black material. Same or similarly, the pad-side right holding face 13b is black in color. In the right side portion 13, for example, a portion including at least the pad-side right holding face 13b may be molded from a black material.

It is highly probable that the light emitter 15 and light detector 16 which are placed at positions avoiding the nail 2c are placed on the side which is close to the pad 2d. According to the above-described configuration, ambient light is absorbed by the pad-side left holding face 12b and the pad-side right holding face 13b, and therefore ambient light can be suppressed from entering the light emitter 15 and light detector 16 which are placed at the above-described positions, respectively. Consequently, the accuracy of calculation of physiological parameter can be further prevented from being lowered.

In the embodiment, the nail-side left holding face 12a is black in color. In the left side portion 12, for example, a portion including at least the nail-side left holding face 12a may be molded from a black material. Same or similarly, the nail-side right holding face 13a is black in color. In the right side portion 13, for example, a portion including at least the nail-side right holding face 13a may be molded from a black material.

Usually, the nail 2c is higher in light reflectance than the pad 2d. According to the above-described configuration, ambient light is absorbed by the nail-side left holding face 12a and the nail-side right holding face 13a, and therefore ambient light can be suppressed from entering from the nail side in which reflection easily occurs, to the light emitter 15 and the light detector 16. Consequently, the accuracy of calculation of physiological parameter can be further prevented from being lowered.

As described above, the probe 1 includes the left side portion 12 and right side portion 13 which cooperate to laterally hold the finger 2. The light emitter 15 is placed in the left side portion 12, and the light detector 16 is placed in the right side portion 13. The hinge portion 14 allows the gap between the left and right side portions 12, 13 to be changed.

According to the configuration, the light emitter 15 and the light detector 16 can be easily positioned at positions which are faced with the side faces of the finger 2, respectively, while avoiding the nail 2c. Therefore, the accuracy of calculation of physiological parameter can be further prevented from being lowered.

As indicated by the broken line in FIG. 1A, the hinge portion 14 may include an elastic member 14a. Examples of the elastic member are a plate spring, a coil spring, and a rubber pad. In this case, the elastic member 14a urges the left side portion 12 and the right side portion 13 so as to cause the portions to approach each other.

According to the configuration, the left side face 2a of the finger 2 can be further fit into the left side portion 12, and the right side face 2b of the finger 2 can be further fit into the right side portion 13. Even in the case where the light emitter 15 and the light detector 16 are placed at positions which are faced with the side faces of the finger 2 that have a large mean curvature, respectively, therefore, stable positioning of the light emitter 15 and the light detector 16 is facilitated. Consequently, the accuracy of calculation of physiological parameter can be further prevented from being lowered.

The above-described embodiment is a mere example for facilitating understanding of the presently disclosed subject matter, and does not limit the presently disclosed subject matter. It is obvious that the embodiment may be adequately changed or improved without departing the spirit of the presently disclosed subject matter, and equivalents are included within the scope of the presently disclosed subject matter.

In the above-described embodiment, the light emitter 15 is placed in the left side portion 12, and the light detector 16 is placed in the right side portion 13. However, the light emitter 15 may be placed in the right side portion 13, and the light detector 16 may be placed in the left side portion 12.

In the above-described embodiment, the light emitter 15 and the light detector 16 are placed at positions which are faced with the pad side of the finger 2, respectively. However, a part of at least one of the light emitter 15 and the light detector 16 may be placed on the nail side of the finger 2. For example, at least one of the light emitter 15 and the light detector 16 may be placed on the dash-dot line C in FIG. 1B.

Figure 2A:
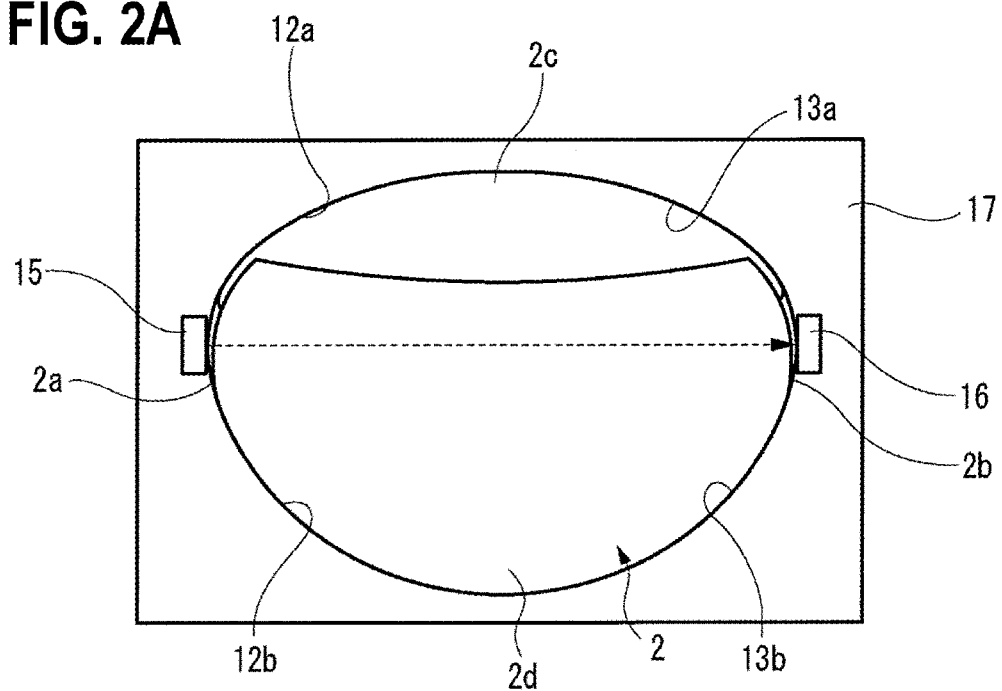
FIGS. 2A and 2B illustrate a modification of the probe.

In the above-described embodiment, the probe 1 includes the left side portion 12 and the right side portion 13. As illustrated in FIG. 2A, however, a configuration including a single housing 17 having a hole into which the finger 2 is to be inserted may be employed.

Also in this case, the nail-side left holding face 12a and the pad-side left holding face 12b are continuous to each other at a position which is faced with the left side face 2a of the finger 2, and the nail-side right holding face 13a and the pad-side right holding face 13b are continuous to each other at a position which is faced with the right side face 2b of the finger 2. Moreover, the nail-side left holding face 12a and the nail-side right holding face 13a are continuous to each other at a position which is faced with the nail 2c, and the pad-side left holding face 12b and the pad-side right holding face 13b are continuous to each other at a position which is faced with the pad 2d.

According to the configuration, the positions of the light emitter 15 and the light detector 16 are not changed before and after attachment of the probe 1 to the finger 2. This facilitates stable positioning of the light emitter 15 and the light detector 16 also in the case where the light emitter 15 and the light detector 16 are placed at positions which are faced with the side faces of the finger 2 that have a large mean curvature, respectively. Therefore, the accuracy of calculation of physiological parameter can be further prevented from being lowered.

Figure 2B:
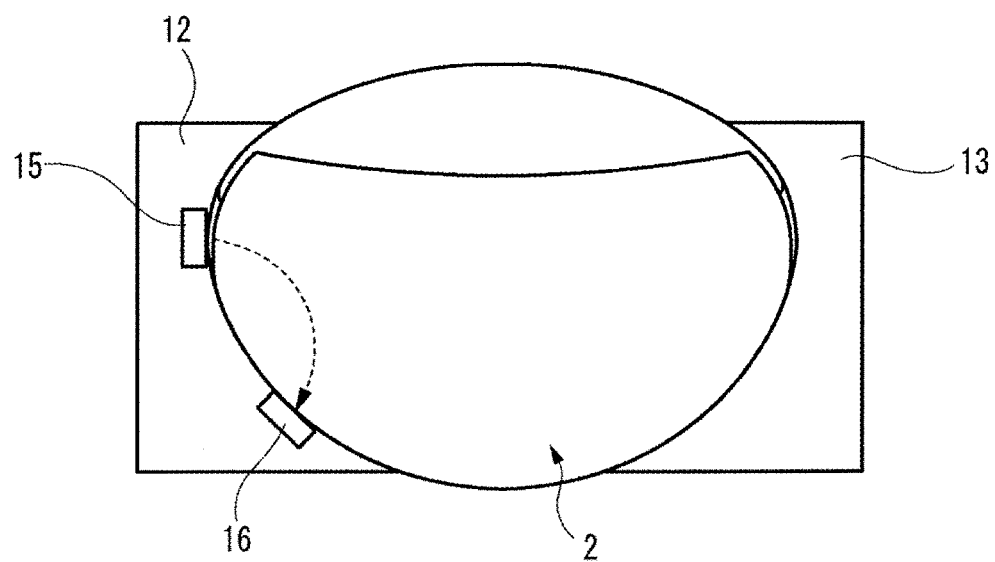

In the above-described embodiment, the light emitter 15 is placed in the left side portion 12, and the light detector 16 is placed in the right side portion 13. As illustrated in FIG. 2B, however, a configuration where both the light emitter 15 and the light detector 16 are placed in the left side portion 12 (or the right side portion 13) may be employed. In this case, the light emitted from the light emitter 15 is reflected from the finger 2, and then detected by the light detector 16.

What is claimed is:
1. A probe which is to be attached to a finger of a subject to acquire a physiological parameter of the subject comprising:
   a left side portion;
   a right side portion;
   a hinge portion that connects the left side portion and the right side portion such that a gap extends longitudinally between the left side portion and the right side portion and is adjustable to receive the finger;
   a light emitter that emits a light beam into the gap toward a location of the gap that is configured to receive the finger;

a light detector that is configured to output a signal corresponding to a light beam that is transmitted through or reflected from the finger;

a first holding face that is formed over each of the left side portion and the right side portion, wherein the first holding face at each of the left side portion and the right side portion has a section configured for being faced with a nail of the finger and another section configured for being faced with a side face of the finger; and a second holding face that also is formed over each of the left side portion and the right side portion, wherein the second holding face at each of the left side portion and the right side portion has a section configured for being faced with a pad of the finger and another section configured for being faced with the side face of the finger, wherein the first and second holding faces at each of the left and right side portions have curvatures extending between top and bottom longitudinally-extending surfaces of the respective left and right side portions, wherein the top and bottom surfaces extend longitudinally between the hinge portion and distal ends of the left and right side portions, wherein at the left side portion, the first holding face and the second holding face are positioned continuous with one another, wherein at the right side portion, the first holding face and the second holding face are positioned continuous with one another, wherein at a cross-sectional plane taken at a point along a longitudinal length of the gap and extending through each of the left side portion and the right side portion and through each of the top and bottom longitudinally-extending surfaces, a shape of the first holding face is different from a shape of the second holding face, wherein the first holding face has a first shape configured for extending along the nail of the finger, and wherein the second holding face has a second shape configured for extending along the finger pad and being different from the first shape, wherein the light emitter is placed at one of the left side portion or the right side portion, wherein the light detector is placed at the other one of the left side portion or the right side portion, wherein a lateral plane extends longitudinally along the gap and extends intermediately between and is separated from the top and bottom surfaces, wherein the light emitter and the light detector each are disposed at a same side of the lateral plane of the respective left and right side portions.

2. The probe according to claim 1, wherein at least one of the light emitter or the light detector is positioned to be faced with the pad side of the finger.

3. The probe according to claim 2, wherein the second holding face is black.

4. The probe according to claim 2,
wherein the left side portion is placed to be faceable with a left side face of the finger,
wherein the right side portion is placed to be faceable with a right side face of the finger,
wherein the light emitter is placed in one of the left side portion or the right side portion, and
wherein the light detector is placed in the other one of the left side portion or the right side portion.

5. The probe according to claim 1, wherein the second holding face is black.

6. The probe according to claim 5, wherein the first holding face is black.

7. The probe according to claim 5,
wherein the left side portion is placed to be faceable with a left side face of the finger,
wherein the right side portion is placed to be faceable with a right side face of the finger,
wherein the light emitter is placed in one of the left side portion or the right side portion, and
wherein the light detector is placed in the other one of the left side portion or the right side portion.

8. The probe according to claim 1,
wherein the left side portion is placed to be faceable with a left side face of the finger,
wherein the right side portion is placed to be faceable with a right side face of the finger,
wherein the light emitter is placed in one of the left side portion or the right side portion, and
wherein the light detector is placed in the other one of the left side portion or the right side portion.

9. The probe according to claim 1, wherein the hinge portion elastically urges the left side portion and the right side portion to cause the left side portion and the right side portion to approach each other.

10. The probe according to claim 1,
wherein the continuous curvatures of the first and second holding faces of the left side portion have mirror symmetry to the first and second holding faces of the right side portion.

11. The probe according to claim 1,
wherein each of the light emitter and the light detector are disposed at the second holding face.

12. The probe according to claim 1,
wherein the light emitter and the light detector each are configured to be disposed at a lateral center line of the finger.

13. The probe according to claim 1,
wherein at least one of the light emitter or the light detector is configured to be deviated from a lateral center line of the finger.

14. A probe which is to be attached to a finger of a subject to acquire a physiological parameter of the subject comprising:

a left side portion;

a right side portion;

a hinge portion that connects the left side portion and the right side portion such that a gap extends longitudinally between the left side portion and the right side portion and is adjustable to receive the finger;

a light emitter that emits a light beam into the gap toward a location of the gap that is configured to receive the finger;

a light detector that is configured to output a signal corresponding to a light beam that is transmitted through or reflected from the finger;

a first holding face that is formed over each of the left side portion and the right side portion, wherein the first holding face at each of the left side portion and the right side portion has a section configured for being faced with a nail of the finger and another section configured for being faced with a side face of the finger; and a second holding face that also is formed over each of the left side portion and the right side portion, wherein the second holding face at each of the left side portion and the right side portion has a section configured for being faced with a pad of the finger and another section configured for being faced with the side face of the finger, wherein the first and second holding faces at each of the left and right side portions have curvatures extending between top and bottom longitudinally-extending surfaces of the respective left and right side portions, wherein the top and bottom surfaces extend longitudinally between the hinge portion and distal ends of the left and right side portions, wherein at the left side portion, the first holding face and the second holding face are positioned continuous with one another, wherein at the right side portion, the first holding face and the second holding face are positioned continuous with one another, wherein at a cross-sectional plane taken at a point along a longitudinal length of the gap and extending through each of the left side portion and the right side portion and through each of the top and bottom longitudinally-extending surfaces, a shape of the first holding face is different from a shape of the second holding face, wherein the first holding face has a first shape configured for extending along the nail of the finger, wherein the second holding face has a second shape configured for extending along the finger pad and being different from the first shape, wherein a lateral plane extends longitudinally along the gap and extends intermediately between and is separated from the top and bottom surfaces, wherein the first holding face is at least majoritively disposed at one side of the lateral plane with the second holding face at least majoritively disposed at an opposite side of the plane, and wherein the first holding face at each of the left and right side portions has a smaller average radius than the second holding face at each of the left and right side portions.

15. The probe according to claim 14, wherein the left side portion is placed to be faceable with a left side face of the finger, wherein the right side portion is placed to be faceable with a right side face of the finger, wherein the light emitter is placed in one of the left side portion or the right side portion, and wherein the light detector is placed in the same one of the left side portion or the right side portion as the light emitter.

16. The probe according to claim 14, wherein the first holding face at each of the left and right side portions has a smaller arc length than the second holding face at each of the left and right side portions.

* * * * *

UNITED STATES PATENT AND TRADEMARK OFFICE
CERTIFICATE OF CORRECTION

PATENT NO. : 10,485,480 B2
APPLICATION NO. : 15/207581
DATED : November 26, 2019
INVENTOR(S) : Yoshinori Ueda It is certified that error appears in the above-identified patent and that said Letters Patent is hereby corrected as shown below:

In the Specification

Column 2, Line 48, "linger" should read --finger--

Signed and Sealed this
Thirty-first Day of March, 2020

Andrei Iancu
*Director of the United States Patent and Trademark Office*